United States Patent

Stanners

[11] Patent Number: 5,593,391
[45] Date of Patent: Jan. 14, 1997

[54] AMPULE SAFETY SYRINGE

[76] Inventor: Sydney D. Stanners, Box 11, 9169 Barnes Pl., Sidney, Canada, V8L 4X7

[21] Appl. No.: 414,736

[22] Filed: Mar. 31, 1995

Related U.S. Application Data

[63] Continuation-in-part of Ser. No. 834,854, Feb. 13, 1992, Pat. No. 5,403,288.

[51] Int. Cl.$^6$ ..................................... A61M 5/00
[52] U.S. Cl. .................... 604/232; 604/110; 604/241; 604/192
[58] Field of Search .................... 604/232, 234, 604/110, 218, 240, 241, 221, 227, 228, 192, 263, 195, 196, 193, 197; 433/80, 87, 89, 90, 116; 215/200, DIG. 3

[56] References Cited

U.S. PATENT DOCUMENTS

| | | | |
|---|---|---|---|
| 3,008,570 | 11/1961 | Roehr et al. | 604/197 |
| 3,292,776 | 12/1966 | Penn | 206/366 |
| 3,739,779 | 6/1973 | Pfleger | 604/241 |
| 3,783,997 | 1/1974 | Brown | 604/201 |
| 3,820,652 | 6/1974 | Thackston | 206/365 |
| 4,425,120 | 1/1984 | Sampson et al. | 604/263 |
| 4,573,976 | 3/1986 | Sampson et al. | 604/263 |
| 4,631,057 | 12/1986 | Mitchell | 604/198 |
| 4,655,751 | 4/1987 | Harbaugh | 604/198 |
| 4,664,656 | 5/1987 | Taddei | 604/241 |
| 4,826,490 | 5/1989 | Byrne et al. | 604/110 |
| 4,859,182 | 8/1989 | Nerli | 128/919 |
| 4,898,590 | 2/1990 | Andors | 604/263 |
| 4,907,968 | 3/1990 | Elsner et al. | 433/80 |
| 4,915,702 | 4/1990 | Haber | 604/198 |
| 4,931,040 | 6/1990 | Haber et al. | 604/110 |
| 4,935,014 | 6/1990 | Haber | 604/110 |
| 4,944,723 | 7/1990 | Haber et al. | 604/228 |
| 5,088,988 | 2/1992 | Talonn et al. | 604/198 |
| 5,112,307 | 5/1992 | Haber et al. | 604/240 |
| 5,112,316 | 5/1992 | Venturini | 604/195 |
| 5,112,327 | 5/1992 | Iinuma et al. | 604/240 |
| 5,122,124 | 6/1992 | Novacek et al. | 604/110 |
| 5,161,681 | 11/1992 | Kemp et al. | 206/364 |
| 5,176,657 | 1/1993 | Shields | 604/232 |
| 5,188,617 | 2/1993 | Linder | 604/232 |
| 5,195,985 | 3/1993 | Hall | 604/232 |
| 5,330,440 | 7/1994 | Stanners et al. | 604/110 |
| 5,403,288 | 4/1995 | Stanners | 604/240 |

*Primary Examiner*—Corrine M. McDermott
*Assistant Examiner*—Ronald K. Stright, Jr.
*Attorney, Agent, or Firm*—Oyen Wiggs Green & Mutala

[57] ABSTRACT

This invention relates to an ampule safety syringe which before and after use protects the needle from exposure. A syringe and ampule combination comprising: (a) an elongated plunger with a thumb press thereon; (b) a finger grip with an opening therein for slidably receiving therethrough the elongated plunger; the finger grip releasably engaging a first end of an ampule; (c) a hollow cylindrical ampule releasably affixed to the finger grip; (d) a plunger moveable piston located and slidably held in the interior of the hollow cylindrical ampule, the piston reciprocating along the longitudinal axis within the interior of the hollow cylindrical ampule; (e) an ampule cap affixed to a second end of the ampule; (f) a hollow needle with first and second pointed ends and having a needle hub between the first and second pointed ends; and (g) a fitting for enabling the needle hub to be releasably affixed to the ampule and cap.

17 Claims, 9 Drawing Sheets

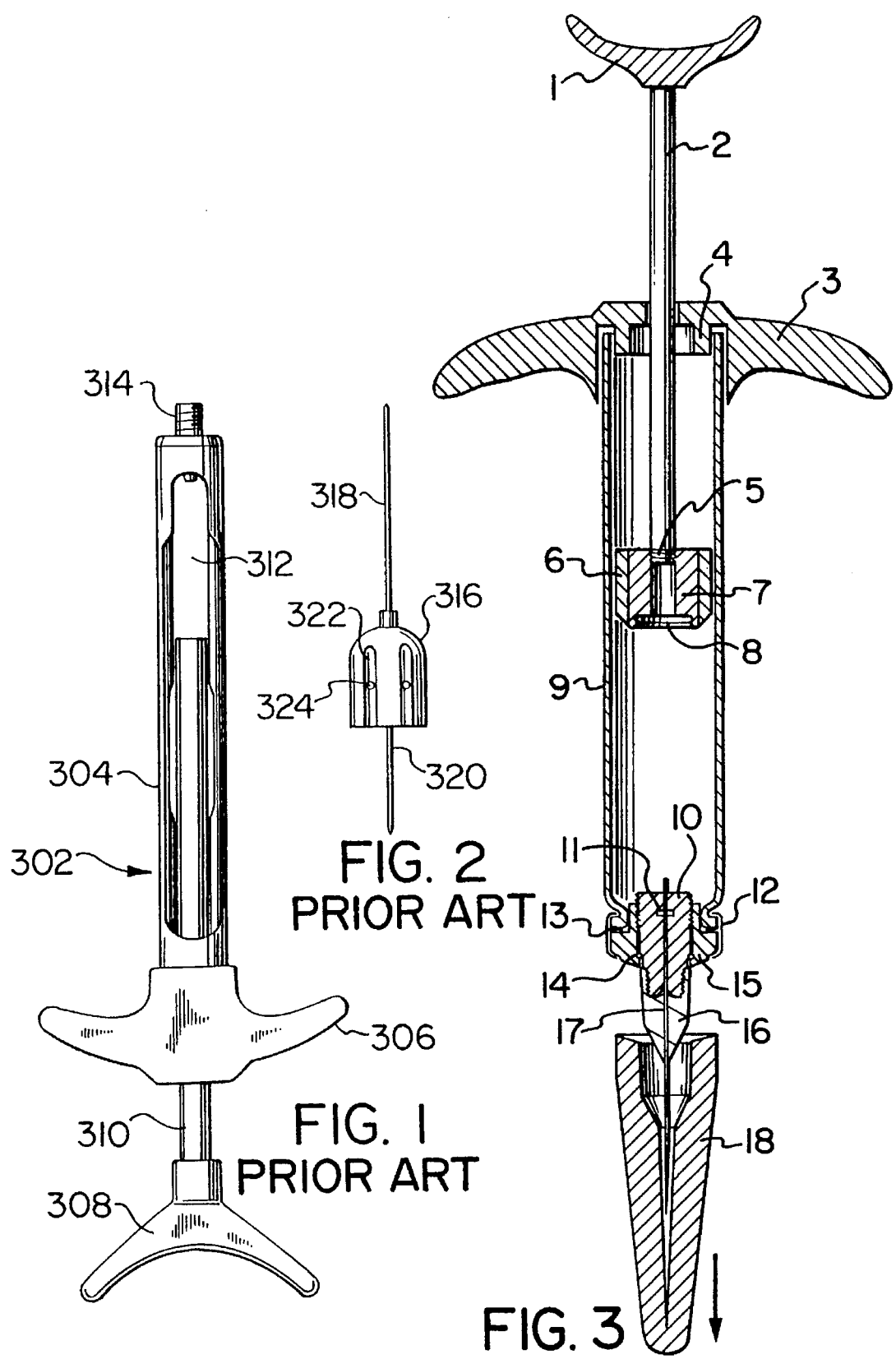

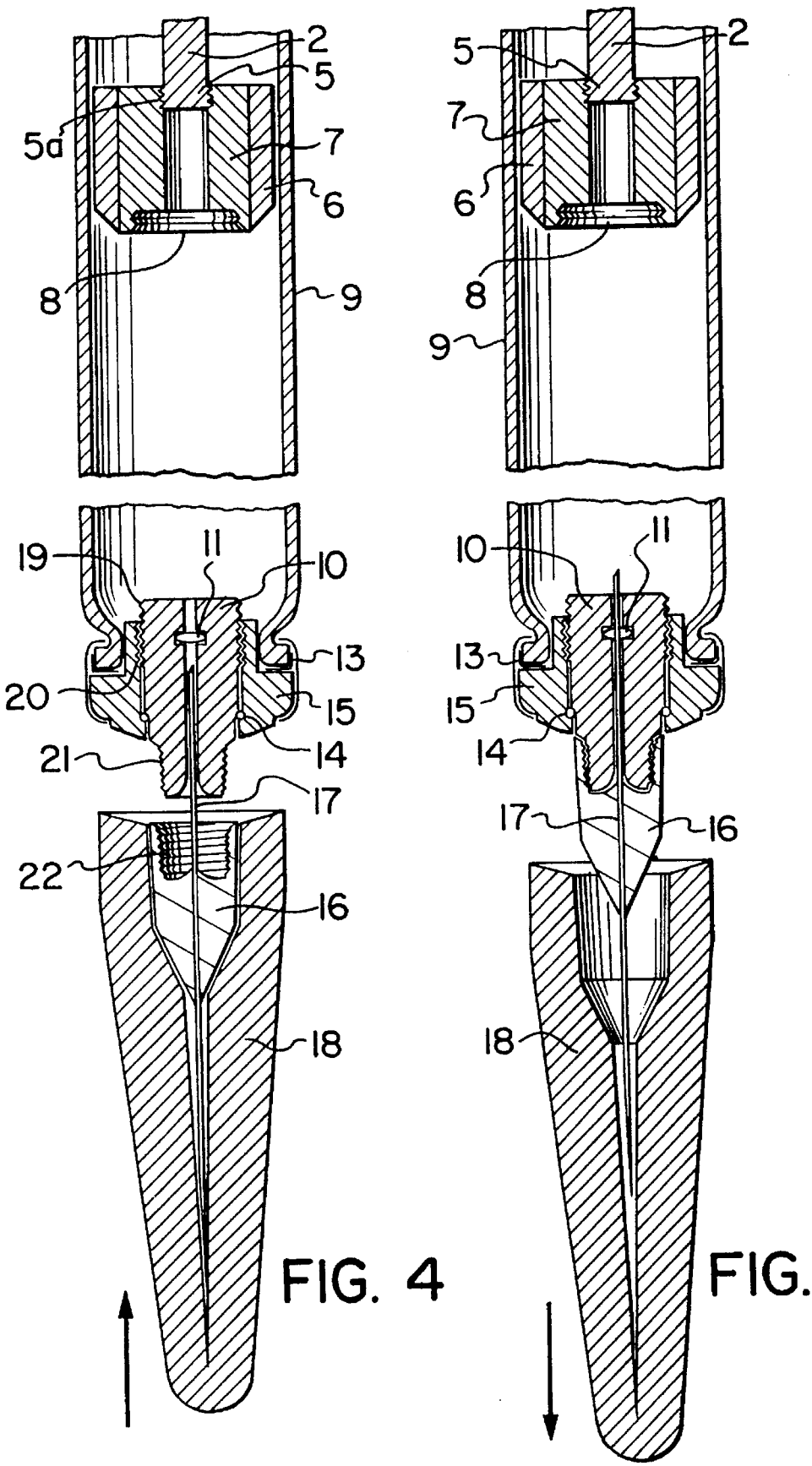

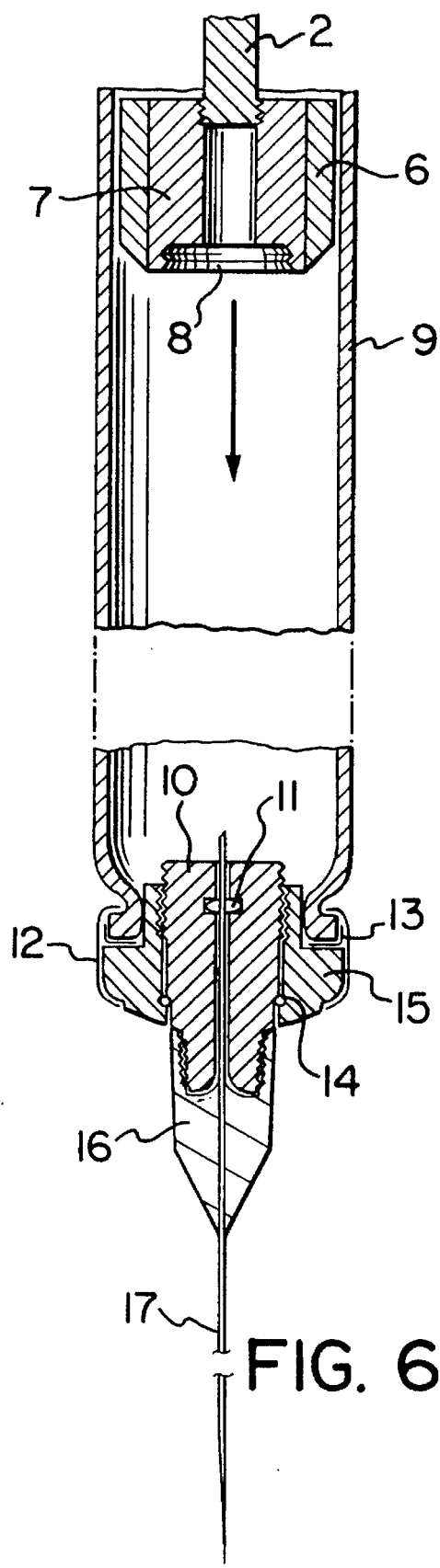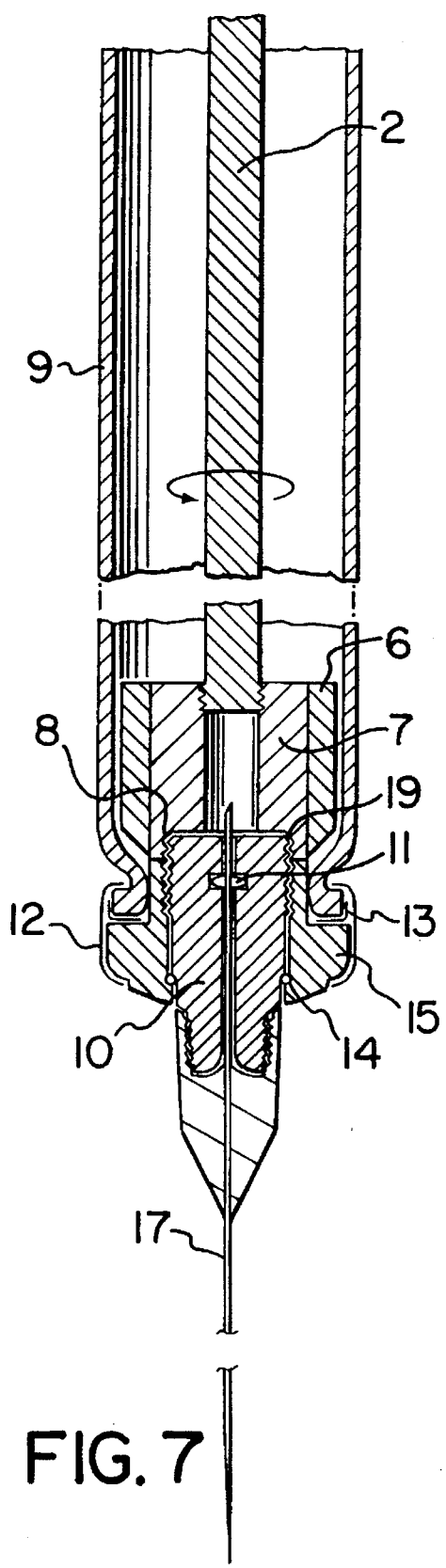
FIG. 6
FIG. 7

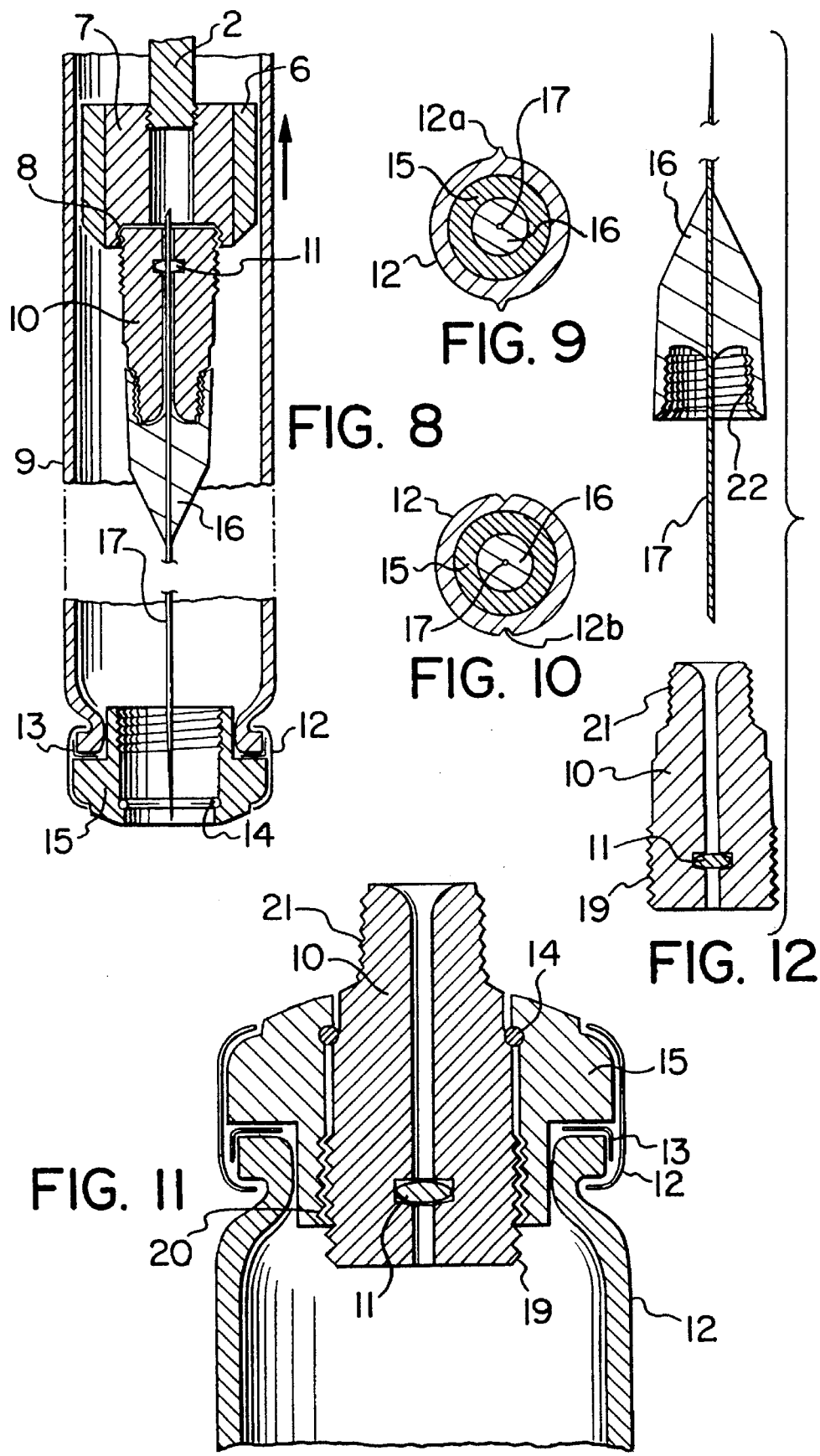

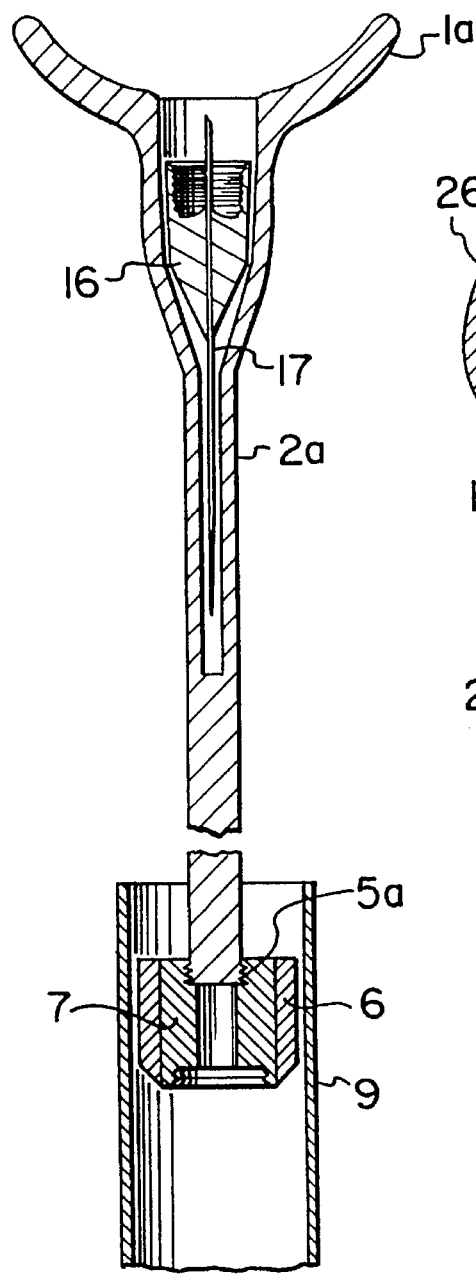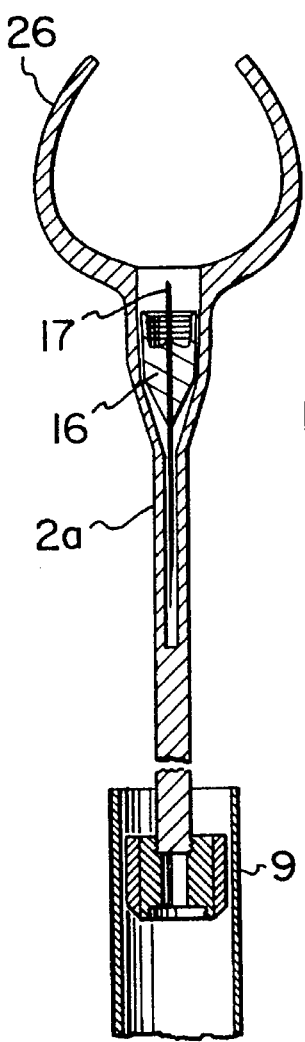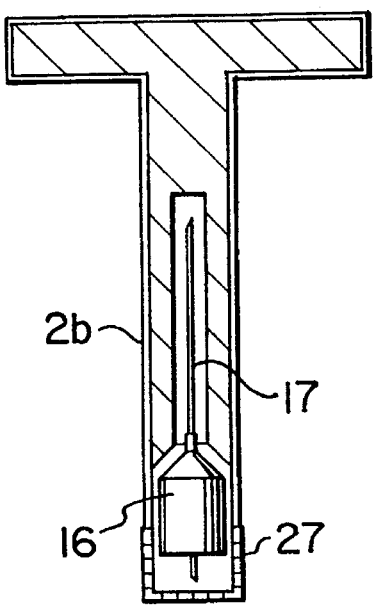
FIG. 16
FIG. 17
FIG. 18

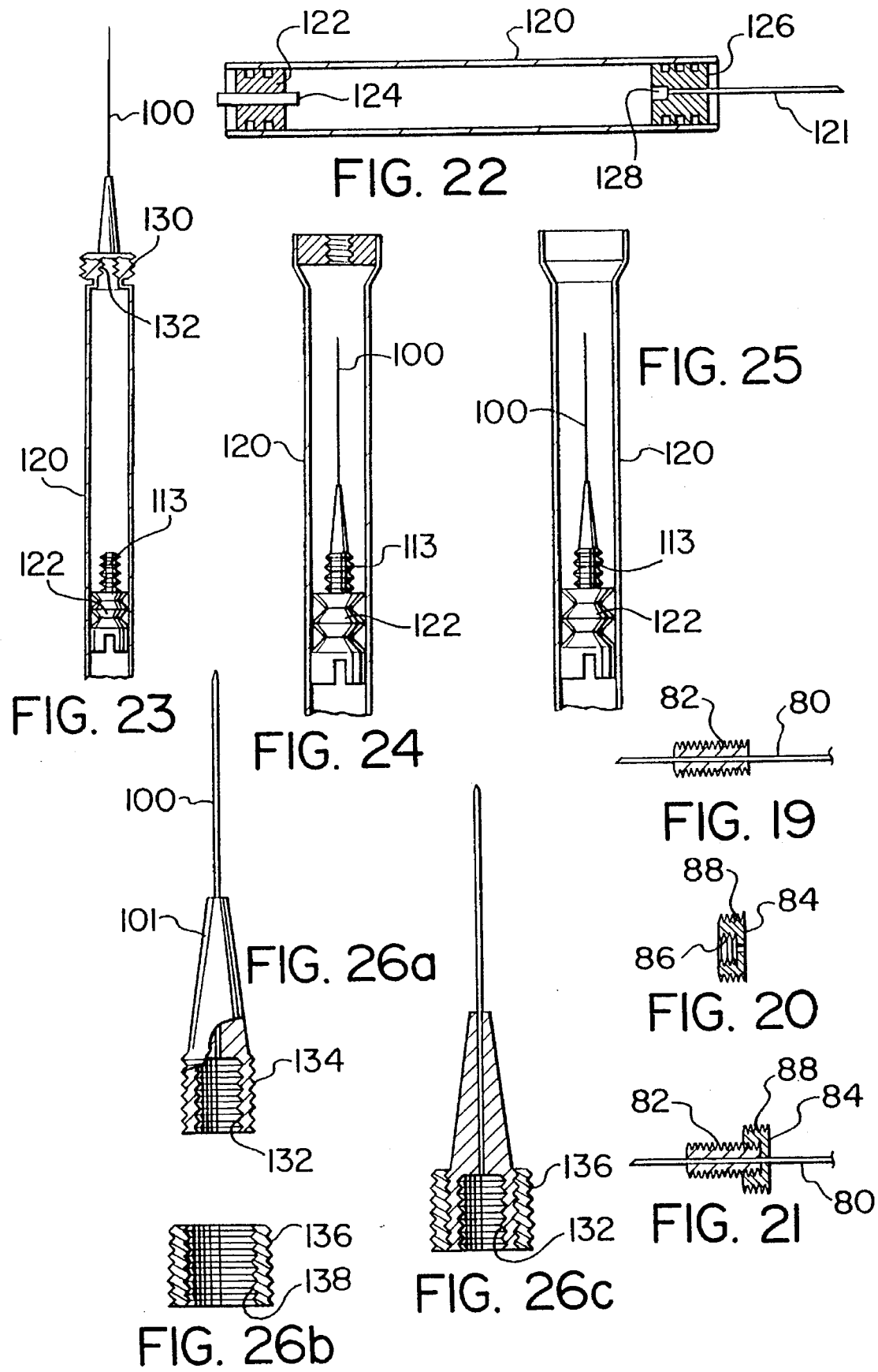

AMPULE SAFETY SYRINGE

This application is a continuation-in-part of application Ser. No. 07/834,854, filed Feb. 13, 1992, and issued on Apr. 4, 1995, as U.S. Pat. No. 5,403,288.

FIELD OF THE INVENTION

This invention relates to an ampule safety syringe which before and after use protects the needle from unwanted exposure. More particularly, this invention pertains to a disposable ampule safety syringe which can be used in place of a conventional dental syringe or a conventional hypodermic syringe. After the ampule safety syringe is used, the needle is withdrawn into the interior of the ampule so that the used needle of the syringe is not exposed during disposal.

BACKGROUND OF THE INVENTION

Needle stick injury is one of the most common occupational health hazards among healthcare professionals. Those involved in both the dental and medical professions are constantly at risk of dangerous patient-to-staff transmission of HIV, hepatitis-B and other blood borne diseases from a contaminated needle.

In recent years, with the increase in dangerous communicable diseases, and particularly the growth of the fatal disease known as AIDS (acquired immune deficiency syndrome), it has become critical to eliminate the incidence of needlestick injuries to personnel in the medical profession, and elsewhere, due to contaminated needles of used syringes. There is a constant risk to the medical profession of contracting the disease of an infected patient by being scratched or pricked from the contaminated needle of a used syringe.

A number of designs of syringes which include features for protecting the exposed needle after use of the syringe have been developed and patented in recent years. The following patents are exemplary and not exhaustive.

U.S. Pat. No. 4,631,057, granted Dec. 23, 1986, Mitchell, discloses an apparatus for injecting a substance into a human or animal. The apparatus includes a body, a needle coupled to the body, and a needle guard mounted on the body for movement from a retracted position in which the guard does not shield the needle to an extended position in which the guard shields the needle. The needle guard can be releasable retained in the retracted position and locked in the extended position. Locking of the needle guard is accomplished by interlocking members carried by the needle guard and by a collar mounted on the body.

U.S. Pat. No. 4,573,976, granted Mar. 4, 1986, Sampson et al., protects a syringe design which has a needle guard mounted on the body of the syringe, the guard being extendible so that it obstructs access to the point of the needle. The guard can be retracted over the barrel of the syringe to expose the point of the needle. Interlocking members on the body and the guard permit the guard to be releasably locked in the retracted or the extended position.

U.S. Pat. No. 4,859,182, Nerli, discloses a dental syringe of the type having a beak for dispensing fluids into an oral cavity. The syringe comprises a sheath, the sheath being a form fitted, generally elongated tube or cylinder adapted to substantially fit over and cover the beak. The sheath is removably attached to the beak, and provides a substantially sterile outer-covering for the beak. The sheath has an open end and a terminal end having an aperture to allow a fluid to be dispensed from the beak and the sheath. The aperture is located near a discharge orifice of the beak through which the fluid is dispensed. The tip is located at the terminal end of the sheath, the tip and the sheath providing a substantially sterile outer-covering for the beak and the discharge orifice. The tip has a valve coincident with the discharge orifice. The valve allows the fluid to be dispensed from the beak and the tip. The valve substantially prevents contaminants from entering or being drawn into the beak through the discharge orifice.

U.S. Pat. No. 4,826,490, Byrne et al., discloses a safety device for a hypodermic needle. Byrne discloses a disposable non-reusable hypodermic needle assembly comprising: a needle support housing having a connector formation for removable attachment with the apparatus; a hypodermic needle supported by the housing for communication with the apparatus by way of the formation, one end portion of the needle projects from the housing remotely from the formation, and a sheath surrounding the housing and mounted thereon for movement in the longitudinal direction of the needle from a first position nearer to the formation and in which first position the needle one end portion is exposed, to a second position further from the formation and in which second position the needle end is enclosed within the sheath.

U.S. Pat. No. 4,907,968, Elsner et al., discloses a dental syringe shield or prophylactic which has a removable disposable dental syringe shield for placement over and in proximate contact with the nozzle of a dental syringe. The design includes an elongated cylindrical portion for fitting over the nozzle of the dental syringe and a barrel portion for fitting over the nozzle securing means of the dental syringe. The design also includes a backsplash collar shield, which fits over the nozzle portion and abuts the front of the base portion of the dental syringe.

U.S. Pat. No. 4,915,702, Haber discloses a shielded safety syringe comprising an inner syringe cylinder having proximal and distal ends, a hypodermic needle supported at and extending outwardly from the distal end, and an outer protective sleeve having proximal and distal ends. The outer sleeve coaxially aligns with an axially advanceable relative to the inner cylinder from a retracted position, where the needle projects outwardly through an opening in the distal end of the sleeve, to an extended position, where the needle is located within and completely surrounded by the sleeve. A first groove is formed in the inner cylinder and locking means are pivotally interconnected with the outer sleeve and rotatable between unlocked and locked conditions, the locking means rotated to the locked condition for receipt within the groove formed in the inner cylinder when the outer sleeve is advanced axially from the retracted to the extended position relative to the inner cylinder.

Patent Cooperation Treaty, international publication no. WO 90/00073 dated 11 Jan. 1990, discloses a single-use injection needle, in particular for dental applications. The syringe comprises a handle including a piston and a support part for a sleeve having an interlocking structure through which the piston extends. The syringe also comprises a syringe body having a tubular end with an inter-locking structure cooperating with that of the sleeve of the handle. The shape is adapted to interlock with the sleeve, and a protecting shell having a locking section capable of covering the tubular end and the sleeve so that they are locked in their interlocking position. The protective shell is adapted for sliding along the syringe body between two extreme positions, i.e. a forward position where it totally covers the injection needle and a pulled-back position where it frees it and covers the interlocked tubular end and sleeve.

Haber et al., U.S. Pat. No. 4,931,040, discloses a dental syringe-carpule (ampule) combination, but the needle is secured to the end of the dental syringe with a slide lock 24, which can be moved vertically from a locked to an unlocked position, and vice versa.

Haber, U.S. Pat. No. 4,935,014, illustrates a dental syringe-carpule (ampule) combination with a cannula (needle) lock involving a pair of jaws which grip the cannula (needle). The carpule of Haber, '014 is conventional and has a blunt end which does not engage by threads with corresponding threads on the needle end of the dental syringe, as is the case with the applicant's invention. In Haber, '014, the ampule head, needle mounting and the needle, after use, are not rotationally unseated in order to withdraw the needle mounting and ampule head into the interior of the ampule.

Linder, U.S. Pat. No. 5,188,617, discloses a dental syringe and an ampule. The apparatus is mainly intended for withdrawing samples from gum pockets. A bent needle, with a threaded hub, is disclosed. However, there is no indication that the ampule 3 is threadedly engaged with the head of the dental syringe. Moreover, it is apparent that the bent needle in Linder is not (and cannot be) retracted into the interior of the ampule, after the needle has been used.

Talonn et al., U.S. Pat. No. 5,088,988, disclose a safety dental syringe which has a protective retractable sleeve. The used needle is protected by a sleeve which is moved to an extended position. Talonn et al. do not show any capability of withdrawing the used needle and head into the interior of the carpule.

Haber et al., U.S. Pat. No. 5,112,307, disclose a dental syringe-carpule-sleeve combination. However, the carpule of Haber et al. has a blunt head, as is conventional. Haber et al. do not disclose any thread mechanism for securing the head of the ampule to the head of the syringe or any mechanism for connecting the plunger of the ampule with the ampule head. Also, the used needle of Haber et al. is protected with a sleeve 4. There is no teaching in Haber et al. of withdrawing the needle into the interior of the carpule after use.

SUMMARY OF THE INVENTION

The invention is directed to an ampule safety syringe combination comprising: (a) an elongated plunger having a first end and a second end, the first end of the plunger having a thumb press thereon, the second end of the plunger having means thereon for releasably engaging a piston; (b) a finger grip with an opening therein for slidably receiving therethrough the elongated plunger, and enabling the plunger to be reciprocally moved through the opening in the finger grip, said finger grip having a means thereon for releasably engaging a first end of an ampule, and enabling the second end of the plunger to penetrate through the opening into the interior of the ampule; (c) a hollow cylindrical ampule having a first end and a second end, the first end of the ampule being proximate to the finger grip and the second end opposite the first end being equipped with an ampule cap; (d) a plunger moveable piston having a first end proximate to and releasably connected to the second end of the plunger and a second end of the piston opposite the first end of the piston, the piston being located and slidably held in the interior of the hollow cylindrical ampule, the piston reciprocating along the longitudinal axis within the interior of the hollow cylindrical ampule, the first end of the plunger extending from the first end of the ampule and the finger grip to the exterior of the ampule opposite the second end of the ampule; (e) an ampule cap affixed to the second end of the ampule in longitudinal axial alignment with and proximate to the second end of the piston and on a side of the second end of the piston opposite the plunger; (f) a hollow needle with first and second pointed ends and having a needle hub between the first and second pointed ends, the needle being located at the second end of the ampule with the second pointed end of the needle protruding from the second end of the ampule and ampule cap; and (g) cap and hub fitting means with a first end proximate the second end of the ampule and a second end, the fitting enabling the needle hub and needle to be releasably affixed to the ampule cap at the second end of the ampule, whereby the first pointed end of the needle penetrates into the interior of the ampule and the second pointed end of the needle extends from the second end of the ampule in a direction opposite to the plunger and the first pointed end of the needle.

The first end and the second end of the piston can be enclosed in the first end of the ampule, the first end of the piston being releasably engaged by engagement means on the second end of the plunger, the fitting being proximate to the first end of the needle, and being penetrated by the first pointed end of the needle, the fitting releasably engaging with the cap at the second end of the ampule, the fitting engaging the second end of the piston when contacted by the piston and being detached from the cap and ampule and withdrawn into the interior of the ampule by withdrawal of the plunger and piston, said piston when engaged by the second end of the plunger and moved by the plunger in the direction of the second end of the needle protruding from the second end of the ampule and fitting, pumping liquid contents from the interior of the ampule through the needle, and engaging the first pointed end of the needle and the fitting at the end of travel of the piston and the plunger towards the second end of the ampule, said piston and plunger when moved by the plunger towards the first end of the ampule away from the second end of the ampule, disengaging the fitting from the cap and withdrawing the fitting and the first and second pointed ends of the needle into the interior of the ampule.

The needle hub of the double pointed needle can have thereon female threads which can be releasably secured to male threads on the second end of the fitting, and the second end of the piston can have threads which can engage corresponding mating threads on the first end of the fitting when the second end of the piston contacts the first end of the fitting and the plunger and the piston are rotated.

The needle hub of the double pointed needle can be a collar which can be located at the mid-section of the double pointed needle, the collar releasably engaging with the second end of the fitting.

The second end of the piston can have formed thereon female threads which can engage male threads on the first end of the fitting, and the first end of the piston can have formed thereon female threads which can releasably engage male threads on the second end of the plunger, and enable the piston to reciprocally move axially within the interior of the ampule and rotate the piston clockwise or counterclockwise about the longitudinal axis.

The second end of the piston can have thereon male threads which can engage corresponding female threads on the first end of the fitting. The ampule cap can have thereon a female thread for releasably engaging the fitting. The ampule cap can be sealed to the second end of the ampule by a seal.

The second end of the fitting can have thereon a male thread which can releasably engage with a corresponding female thread on the first end of the hub of the needle. The second end of the fitting can have thereon a female thread which can releasably engage with a corresponding male thread on the first end of the hub of the needle.

The hub of the double pointed needle can have a male thread on the exterior thereof for releasable engagement with a corresponding female thread on the fitting, said fitting having a female thread thereon for engaging with a corresponding male thread formed on the second end of the piston.

The syringe can include a releasable needle cap over the hub and needle, It can include a resilient liquid seal between the exterior of the piston and the interior of the ampule and annular means on the finger grip for releasably engaging the first end of the ampule. The syringe can include a liquid seal between the fitting and the needle, a sealing cap holding the ampule cap and the second end of the ampule together, a liquid seal between the ampule cap and the fitting and a liquid seal between the ampule cap and the second end of the ampule.

DRAWINGS

In drawings which depict specific embodiments of the invention, but which should not be construed as restricting or limiting the scope of the invention in any way:

FIG. 1 illustrates a front perspective view of a typical prior art dental syringe constructed of stainless steel.

FIG. 2 illustrates a front view of a typical dual-needle assembly used by a dentist in the conventional dental syringe illustrated in FIG. 1.

FIG. 3 illustrates a front section view of the ampule safety syringe of the invention.

FIG. 4 illustrates an enlarged front section view of the piston cap and needle cap part of the ampule syringe, with the cap and needle being mounted on the needle hub-cap fitting.

FIG. 5 illustrates an enlarged front section view of the piston cap and needle cap part of the ampule syringe, with the cap and needle being withdrawn from the needle hub-cap fitting.

FIG. 6 illustrates an enlarged front section view of the piston cap and needle cap part of the ampule syringe, with the cap and needle being withdrawn from the needle hub-cap fitting, and the ampule syringe ready for use by advancing the thumb press, plunger and piston.

FIG. 7 illustrates an enlarged front section view of the piston cap and needle cap part of the ampule syringe, with the cap and needle withdrawn from the needle hub-cap fitting, and the ampule syringe after use by advancing the thumb press, plunger and piston after use, with the piston core being rotated to engage the needle hub-cap fitting.

FIG. 8 illustrates an enlarged front section view of a part of the ampule syringe with the plunger and the engaged needle hub-cap fitting and needle hub being withdrawn into the interior of the ampule.

FIG. 9 illustrates an end section view of a first embodiment of the ampule cap seal, cap, needle hub and needle assembly.

FIG. 10 illustrates an end section view of a second embodiment of the ampule cap seal, cap, needle hub and needle assembly.

FIG. 11 illustrates an enlarged front section view of the needle hub-cap fitting, cap and ampule assembly.

FIG. 12 illustrates an enlarged front section, exploded view of the needle hub and needle hub-cap fitting assembly.

FIG. 16 illustrates a side section view of an alternative second embodiment of plunger including a cavity at the thumb press end for holding a needle and hub combination.

FIG. 17 illustrates a front section view of an alternative third embodiment of plunger with a hollow therein at the thumb press end for holding a needle and hub combination, and curved finger grips.

FIG. 18 illustrates a front section view of an alternative fourth embodiment of plunger including a cavity at the piston engaging end for holding a needle and hub combination.

FIG. 19 illustrates a side section view of a two-pointed dental needle with a threaded collar about the mid-section of the needle.

FIG. 20 illustrates a side section view of a threaded shoulder for a two-pointed dental needle.

FIG. 21 illustrates a side section view of a threaded shoulder engaged over a threaded collar of a two-pointed dental needle.

FIG. 22 illustrates an alternative embodiment of an ampule with a plunger at one end and a seal at the opposite end.

FIG. 23 illustrates a front section view of an alternative embodiment of ampule with an ampule cap and needle.

FIG. 24 illustrates a front section view of an alternative embodiment of ampule with the needle withdrawn into the interior of the ampule.

FIG. 25 illustrates a front section view of an alternative embodiment of ampule with the needle withdrawn into the interior of the ampule.

FIGS. 26a, 26b and 26c illustrate in succession a front section view of an alternative embodiment of needle and needle housing with threads which engage with threads of an ampule cap, to form the embodiment illustrated in FIG. 26c.

DETAILED DESCRIPTION OF SPECIFIC EMBODIMENTS OF THE INVENTION

Figure 13:
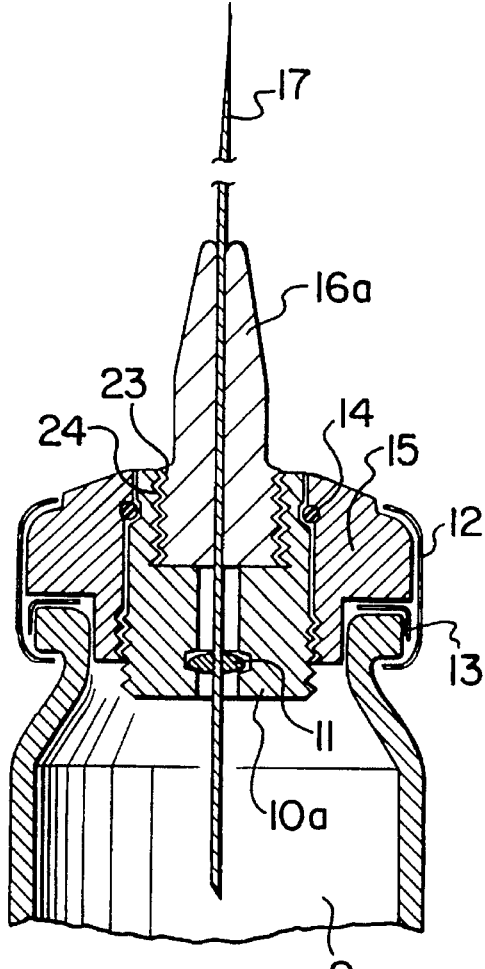
FIG. 13 illustrates an enlarged front section view of an alternative second embodiment of needle hub-cap fitting and cap assembly, with male and female threads reversed.

The disclosed ampule safety syringe is designed to be readily assemblable, inexpensive, disposable, and to keep physical exposure to the needle point of a syringe at an absolute minimum at all times. This provides protection to a handler both at the time of the injection and during subsequent disposal of the used needle.

A detailed discussion of specific embodiments of ampule safety syringe of the invention follows in relation to the drawings. Referring to the drawings, FIG. 1 illustrates for reference purposes a front perspective view of a typical dental syringe available on the market. The dental syringe 302 is usually constructed of stainless steel and has a barrel 304, to which is attached a pair of finger grips 306. Inserted into the interior of the hollow barrel is a piston 310 which has at the end thereof a thumb grip 308. The cavity 312 formed between the end of the piston 310 opposite the thumb grip 308, and a portion of the barrel 304 is designed to hold a conventional anaesthetic ampule. The ampule contains an anaesthetic such as Novocaine. At the end of the barrel 304 opposite finger grip 306, there is positioned a male thread needle base which is adapted to receive the female threads inside the housing of a typical double needle used with a dental syringe.

FIG. 2 illustrates a front view of a typical dual-needle assembly used by a dentist in a conventional syringe 302 illustrated in FIG. 1. As seen in FIG. 2, the typical dual-needle assembly consists of a hollow needle housing 316, which has formed in the interior thereof female threads adapted to fit with male threads on needle base 314 of the dental syringe 304. The housing has at one end thereof an injection needle 318, which the dentist uses to penetrate into the appropriate nerves in a patient's mouth in order to "freeze" the gum and tooth nerves prior to performing dental work on the patient's teeth. At the opposite end, there is an ampule needle 320.

In the conventional case, the dentist screws housing 16 over needle base 314, whereupon, ampule needle 20 penetrates into an end of the ampule which is positioned inside ampule cavity 312. The end of the typical ampule is constructed of rubber so that it is seals the ampule, but can be easily penetrated by the ampule needle 320. Once the ampule needle 320 has penetrated into the interior of the ampule, the dentist can inject anaesthetic through needle 318 by depressing thumb grip 308. The depiction of needle housing 316 is not entirely conventional because, as illustrated in FIG. 2, the exterior of the housing 316 has formed therein a set of vertically extending housing grooves 322. The grooves 22 have formed therein, about midway along the length of the groove 322, appropriate circular pockets 324.

FIG. 3 illustrates a front section view of the ampule safety syringe of the invention. The ampule syringe comprises, in assembled form, a thumb press 1 suitable for pressing with the administrator's thumb, said thumb press 1 being connected to an elongated plunger 2. The elongated plunger 2, which is in the form of a rod, penetrates through a hole in a finger grip 3, which is ergonomically shaped to be gripped by a pair of fingers of the administrator of the medication in the ampule of the syringe. The finger grip 3 has on the bottom interior thereof an annular shaped ampule grip lip 4, which with the finger grip 3 forms an annular groove which is designed to engage a first end of a tube-like ampule 9. The combination of the finger grip 3 with the grip lip 4 and the plunger 2 penetrating the finger grip 3, secures the first end of the ampule 9 in a snug manner. The end of the plunger 2 opposite the thumb press 1 has a male plunger thread 5, which engages with a corresponding female thread formed in the adjacent end of a piston core 7. The piston core 7 has around the circumference thereof adjacent the interior wall of the ampule 9 a resilient piston seal 6, typically formed of resilient rubber or plastic, which provides a liquid tight slidable fit between the piston core 7 and the interior wall of the ampule 9.

The piston core 7 has formed at the end opposite the plunger engaging end a female piston thread 8 which is adapted by rotation to engage with a corresponding male thread on the adjacent end of needle hub-cap fitting 10. The needle hub-cap fitting 10 engages by male threads with female threads in the interior of hollow cap 15, which fits on the carpule 9 at the end opposite the finger grip 3.

Needle hub-cap fitting 10 and circumferential cap 15 are held in place on the end of carpule 9 by an ampule cap seal covering 12. A double ended needle 17 extends longitudinally through the interior of the needle hub-cap fitting 10 and is sealed by seal 11 in the interior of the fitting 10. A resilient needle hub-cap seal 14 seals the intersection between the needle hub-cap fitting 10 and the cap 15. An ampule seal ring 13 seals the intersection between the cap 15 and the cap adjacent end of the carpule 9. Needle 17 is held at its mid-section by needle hub 16, which engages by female threads with the male threads on an end of needle hub-cap fitting 10. A needle cap 18 fits over and protects the free end of the needle 17, which extends from the needle hub 16.

FIG. 4 illustrates an enlarged front section view of the piston cap and needle cap part of the ampule syringe, with the cap and needle being mounted on the needle hub-cap fitting. As seen in FIG. 4, in detail, the male plunger threads 5 of plunger 2 have been engaged in corresponding female threads 5a of piston core 7. A female piston thread 8 is formed in the opposite end of the piston core 7 from plunger thread 5 and female plunger thread 5a.

The end of the needle hub-cap fitting 10, facing piston thread 8, protrudes somewhat and has formed on the exterior thereof a male thread 19. A portion of this needle hub-cap fitting male thread 19 engages with a corresponding mating female thread 20 formed in the interior opening of cap 15. The end of the needle hub-cap fitting 10, opposite to the end carrying male threads 19, protrudes somewhat and has formed around the exterior circumference thereof male hub engaging threads 21. These male threads 21 correspond to and are adapted to engage with female threads 22 which are formed in the interior of needle hub 16.

As illustrated in FIG. 4, by means of the directional arrow, the cap 18, which encloses the needle 17-hub 16 combination, is moved towards the cap 15, fitting 10 end of the ampule syringe so that the free end of the needle 17 penetrates through the interior elongated opening in needle hub-cap fitting 10, and ultimately penetrates through seal 11, into the interior of the ampule 9.

FIG. 5 illustrates an enlarged front section view of the piston cap and needle cap part of the ampule syringe, with the cap and needle being withdrawn from the needle hub-cap fitting. As seen in FIG. 5, as indicated by the directional arrow, once the needle 17 and hub 16 have been engaged by screwing female threads 22 on the interior of hub 16 over male threads 21 extending from the free end of the needle hub-cap fitting 10, the needle 17 penetrates through the interior of the fitting 10 and through seal 11 into the interior of the ampule 9. The cap 18 is then withdrawn from the needle 17 hub 16 combination to expose the free end of the needle 17, which is sharply pointed to penetrate the flesh of a patient. The medicinal contents to be injected into the patient are contained in ampule 9, which is pre-filled at the manufacturer's plant, and can come as part of the plunger 2, finger grip 3, and needle 17, cap 18 combination, or separately. The ampule 9 in each case, complete with piston core 7, piston seal 6, fitting 10 and cap 15, is assembled and filled at the manufacturer's plant.

The particular medicinal agent required by the physician or medicine administrator is prepackaged at the manufacturer's plant. For instance, if a dentist wishes to purchase syringes for injection of a "freezing" in the mouth of a patient, he or she will order from the manufacturer a specified number of carpules containing the appropriate freezing agent. The other components making up the ampule syringe can also be purchased separately or as part of the overall package. The needles are used only once and are then discarded. Likewise, the plunger and the cap are also used only once and then discarded. The whole unit is inexpensive and readily disposable.

FIG. 6 illustrates an enlarged front section view of the piston cap and needle cap part of the ampule syringe, with the cap and needle being withdrawn from the needle hub-cap fitting, and the ampule syringe ready for use by advancing the thumb press, plunger and piston. As indicated by the directional arrow, the plunger 2 and piston core 7, piston seal 6 combination, when the administrator uses the ampule syringe to inject medication into a patient, moves by thumb pressure towards the fitting 10, cap 15 and needle hub 16-needle 17 combination. The liquid contents held in the interior of the ampule 9 are thereby expelled through the interior of needle 17 into the patient.

FIG. 7 illustrates an enlarged front section view of the piston cap and needle cap part of the ampule syringe, with the cap and needle withdrawn from the needle hub-cap fitting, and the ampule syringe after use by advance of the thumb press, plunger and piston. Once the medication has been injected into the patient through needle 17, and the piston core 7 touches the protruding adjacent end of fitting 10, the plunger 2 is rotated as indicated by the directional arrow to engage the female threads 8 with matching male threads 19 on the fitting 10. Once the threads are engaged, then by continued rotation of the plunger 2, or alternatively, counter-rotation, depending on thread direction, the part of the threads 19 that engage the fitting 10 with cap 15 disengage, and the piston 7, fitting 10, hub 16 combination is then ready as a unit for withdrawal into the interior of the ampule 9.

FIG. 8 illustrates an enlarged front section view of a part of the ampule syringe with the plunger and the engaged needle hub-cap fitting and needle hub being withdrawn into the interior of the ampule. As illustrated in FIG. 8, the piston core 7, fitting 10, hub 16, needle 17 combination has been withdrawn into the interior of the ampule 9, by withdrawing plunger 2 in the direction indicated by the directional arrow. In this way, the used needle 17 is withdrawn into the interior of the ampule 9 and is no longer exposed for potentially hazardous accidental penetration of a handler disposing of the ampule syringe.

FIG. 9 illustrates an enlarged end section view of the ampule cap seal 12, cap 15, needle hub 16 and needle 17 assembly. FIG. 10 illustrates an end section view of an alternative embodiment of the ampule cap seal 12, cap 15, needle hub 16 and needle 17 assembly. The projections 12a in FIG. 9, and the grooves 12b in FIG. 10 are optional, and aid in preventing unwanted rotation of an ampule in a dental syringe (see FIG. 14).

FIG. 11 illustrates an enlarged front section view of the needle hub-cap fitting, cap and ampule assembly. In particular, FIG. 11 illustrates in detail male threads 19 on the needle hub-cap fitting 10, female cap fitting engaging threads 20 on the interior opening of the cap 15, and the male hub engaging threads 21 on the fitting 10. Ampule seal ring 13 and ampule cap seal covering 12 are also illustrated in detail. The ring 13 is typically formed of a resilient material for providing a good seal between the top rim of the ampule 9 and the cap 15. Seal covering 12 can be stamp formed of a light metal or plastic and holds the cap 15 and ampule 9 together.

FIG. 12 illustrates an enlarged front section, exploded view of the needle hub and needle hub-cap fitting assembly. Specifically, FIG. 12 illustrates female fitting engaging threads 22 on the interior of the hub 16, which are adapted to engage male threads 21 on fitting 10.

FIG. 13 illustrates an enlarged front section view of an alternative embodiment of needle hub-cap fitting and cap assembly, with male and female threads reversed. As seen in FIG. 13, fitting 10a had been modified somewhat so that it has female threads 24 which mate with corresponding male threads 23 on hub 16a. The decision whether to use the thread arrangement illustrated in the alternative embodiment in FIG. 13, rather than the thread arrangement illustrated in the previous drawings, is a matter of choice for the manufacturer.

Figure 14:
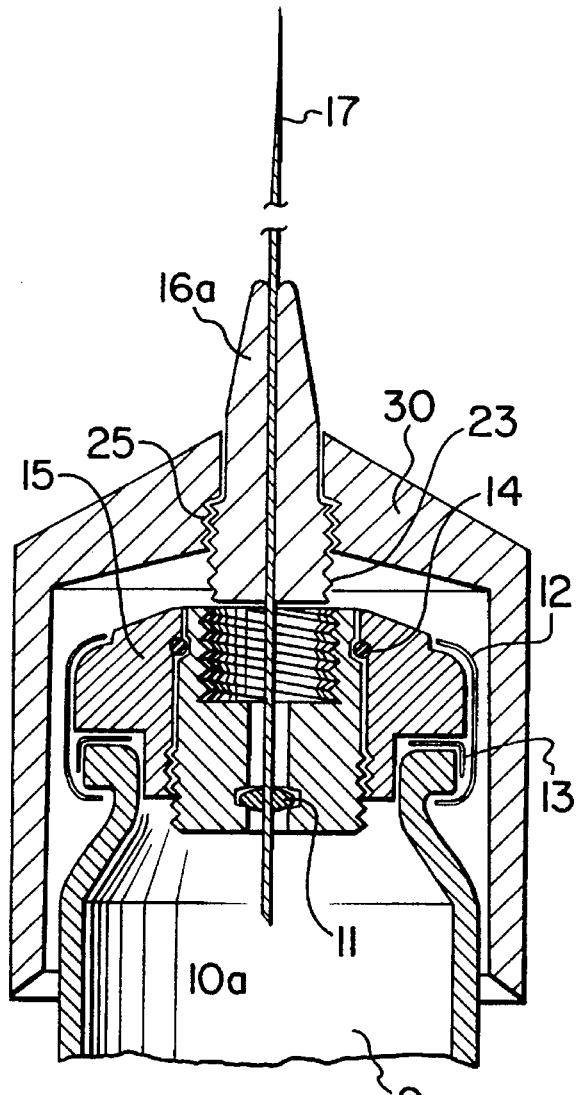
FIG. 14 illustrates an enlarged front section view of an alternative third embodiment of needle hub-cap fitting and cap assembly, with male and female threads reversed with the ampule fitting within the barrel of a dental syringe and the needle hub engaged with the barrel of the dental syringe.

FIG. 14 illustrates an enlarged front section view of a further alternative embodiment of needle hub-cap fitting and cap assembly, with male and female threads reversed with the ampule fitting within the barrel of a dental syringe and the needle hub engaged with the barrel of the dental syringe. As seen in FIG. 14, male threads 23 on hub 16a engage with female threads 25 formed at the top opening of the metal barrel 30 of the standard dental syringe.

FIGS. 15a through 15f illustrate in sequence the manner in which the components of the ampule safety syringe are assembled together and the syringe is used by the administrator, and after use, the needle is withdrawn into the ampule and the plunger disengaged.

Figure 15A:
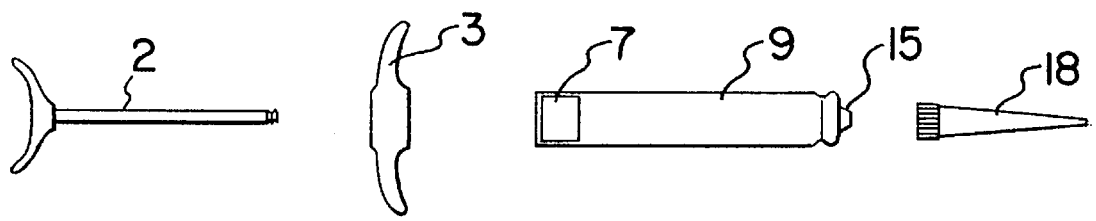
FIG. 15a illustrates a front exploded partial section view of the components of the ampule syringe, prior to assembly as a unit.
Figure 15B:
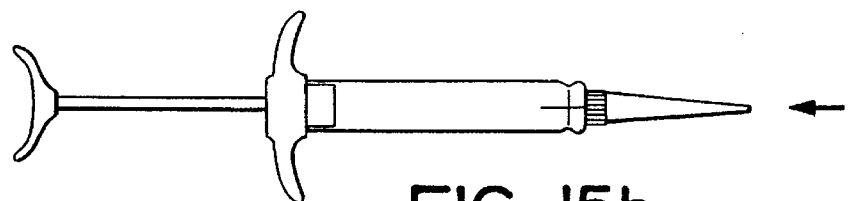
FIG. 15b illustrates a front partial section view of the components of the ampule syringe assembled together.
Figure 15C:
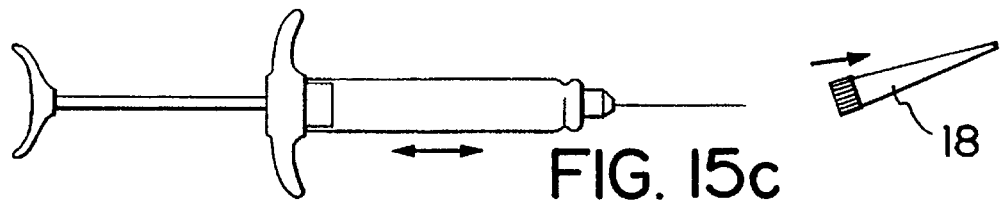
FIG. 15c illustrates a front partial section view of the ampule syringe with the cap removed, and the syringe ready for use.
Figure 15D:
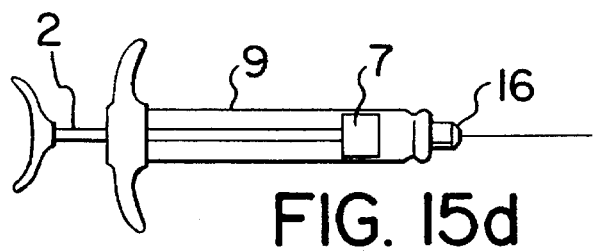
FIG. 15d illustrates a front patial section view the ampule syringe after the contents of the ampule have been injected into a patient, and the plunger has been pressed into the interior of the ampule.
Figure 15E:
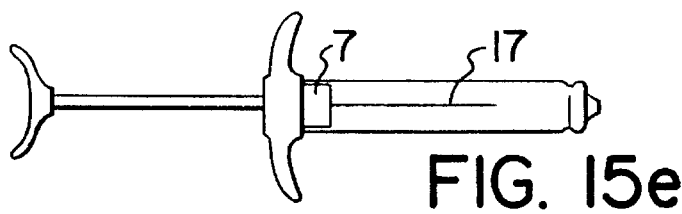
FIG. 15e illustrates a front partial section view of the ampule syringe with the needle withdrawn into the interior of the ampule by the piston.
Figure 15F:
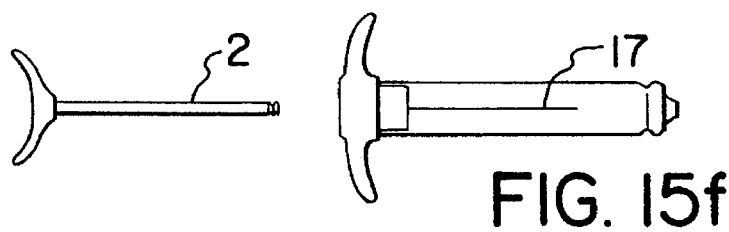
FIG. 15f illustrates a front partial section view of the ampule syringe with the needle withdrawn by the piston into the interior of the ampule, and the plunger disengaged from the piston.

FIG. 15a illustrates a front exploded partial section view of the plunger, finger grip, piston, ampule, cap and needle cap components 2, 3, 7, 9, 15 and 18 of the ampule syringe. FIG. 15b illustrates a front partial section view of the components of the ampule syringe assembled together. FIG. 15c illustrates a front partial section view of the ampule syringe with the cap 18 removed, and the ampule syringe ready for use. FIG. 15d illustrates a front partial section view the ampule syringe after the medicinal contents of the ampule have been injected into a patient, and the plunger 2 has been pressed into the interior of the ampule 9 to exhaust the contents of the ampule. After that, the plunger 2 is rotated and the piston 7 engages the hub 16 of the needle. FIG. 15e illustrates a front partial section view of the ampule syringe with the needle 17 withdrawn into the interior of the ampule by the piston 7. FIG. 15f illustrates a front partial section view of the ampule syringe with the needle 17 withdrawn by the piston into the interior of the ampule, and the plunger 2 disengaged from the piston. The ampule syringe can then be disposed of.

FIG. 16 illustrates an enlarged side section view of an alternative design of plunger including a cavity at the thumb press end for holding a needle and hub combination. As illustrated in FIG. 16, the modified plunger 2a at the end proximate the thumb press 1a has a hollow formed therein adapted for receiving a needle hub 16 and needle 17 combination. This arrangement presents a useful way to package the needle hub and needle combination 16, 17 and eliminates the need to have a separate needle cap 18 as illustrated in prior drawings. It may be more economical to package the hub and needle combination in the form illustrated in FIG. 16, rather than in a cap 18 as illustrated in prior drawings. As seen in FIG. 16, the administrator wishing to use the ampule syringe before engaging the plunger 2a with the piston core 7, inverts the plunger 2a in a manner similar to that shown in FIGS. 4 and 5, and engages the hub 16 and needle 17 with the male threads 21 of the fitting 10 (not visible in FIG. 16). Then, once the needle hub, needle combination 16, 17 is engaged, the administrator withdraws the plunger 2a off the hub 16 and needle 17, moves it to the opposite end of the carpule 9, and then by rotation engages threads 5a with the interior threads of piston core 7.

FIG. 17 illustrates a front partial section view of an alternative embodiment of plunger 2a with a hollow therein at the thumb press end for holding a needle and hub combination. The embodiment illustrated in FIG. 17 is a variation on the embodiment illustrated in FIG. 16. The thumb press 26, as seen in FIG. 17, has curved sides which are adapted to engage the thumb of an administrator of the ampule syringe. The thumb grips 26 fit around a portion of the thumb of the administrator and enable the administrator to aspirate the ampule syringe by raising or depressing the thumb in a reciprocating fashion.

FIG. 18 illustrates a front partial section view of an alternative design of plunger 2b including a cavity at the piston engaging end for holding a needle 17 and hub 16 combination. The plunger 2b illustrated in FIG. 18 has an opening at the piston proximate end of the plunger rather than at the thumb press end, as illustrated previously in FIG. 16. A cap 27 fits over the open end of the plunger 2b.

FIGS. 19, 20 and 21 illustrate an embodiment of the invention wherein the needle is equipped with a collar and a shoulder adapted to mate with the end of a dental syringe, or the ampule syringe. As seen in FIG. 19, the two-pointed needle 80 has a male thread collar 82 around its mid-section. FIG. 20 illustrates a side section view of a shoulder 84 which is of a general cup-shape, with a female thread 86 on the interior circumference thereof, and a male thread 88 on the exterior wall thereof. The female thread 86 is adapted to engage with the male thread on the exterior of the collar 82. FIG. 21 illustrates the shoulder 84 and the collar 82 engaged on needle 80.

FIG. 22 illustrates a side partial section view of a further embodiment of an ampule 120 which is adapted so that the needle 121 can be withdrawn into the interior of the ampule 120 after use. One end of the ampule 120 is equipped with a plunger piston 122, which has a plastic key 124 penetrating through it. The opposite end of the ampule 120 has a seal 126 which has a key receptacle 128 formed therein. When the needle 121 penetrates into the interior of seal 126, the seal 126 grips the end of the needle 121. Subsequently, when the dentist pushes the plunger 122 towards the needle 121 and seal 126, in order to pump the contents of the ampule 120 through the needle 121, the plunger 122 eventually meets with seal 126 so that plastic key 124 engages with key receptacle 128. The seal 126 is designed so that it can be readily withdrawn into the interior of ampule 120, after the anaesthetic is pumped out. The seal 126 is prevented from escaping the interior of ampule 120 by the conventional syringe housing (not shown) and suction created by the filled ampule 120 if the seal 126 attempts to escape. However, when plunger 122 and key 124 contact the seal 126, and key receptacle 128, after the anaesthetic is exhausted, a connection is made which is sufficiently strong that seal 126, with needle 121, can be withdrawn into the interior of ampule 120 by withdrawing plunger 122. Once the needle 121 is fully withdrawn into the interior ampule 120, the ampule and the used needle 121, and other components of the ampule syringe can be discarded without fear of puncture by the exposed pointed end of needle 121.

FIG. 23 illustrates a front section view of a further embodiment of ampule with an ampule cap and needle. As seen in FIG. 23, the ampule 120 is fitted at its top with an ampule cap 130, which has male threads around the circumference. These threads are adapted to screw into a conventional dental syringe (not shown but see FIG. 14) which has had the adapter coupling removed. The internal female threads 132 are adapted to be engaged with the male threads 113 at the top end of piston 122. The injection needle 100 is engaged at its base with the top of ampule cap 130. After use, that is, when the piston 122 has been fully advanced through the interior of the ampule 120, thereby forcing the anaesthetic or medicinal fluid out through needle 100, male threads 113 are rotated into female threads 132, thereby enabling the needle housing and needle 100 to be withdrawn into the interior of the ampule 120 by withdrawing the piston 122.

FIG. 24 illustrates a front partial section view of an ampule 120 with the needle 100 withdrawn into the interior of the ampule. As seen in FIG. 24, the piston 122 has been withdrawn after male threads 113 are engaged so that the needle 100 and housing can be withdrawn into the interior of the ampule 120. FIG. 25 illustrates a front partial section view of an alternative embodiment of ampule with the needle withdrawn into the interior of the ampule 120.

FIGS. 26a, 26b and 26c illustrate in succession a front partial section view of a needle and needle housing with threads which engage with threads of an ampule cap, to form the embodiment illustrated in FIG. 26c. As seen in FIG. 26a, the needle 100 and needle housing 101, have at the base thereof male threads 134 on the exterior, and female threads 132 on the interior. FIG. 26b shows in detail the construction of the threaded ampule cap with male threads 136 on the exterior, and female threads 138 on the interior. When the male threads 134 of the needle housing 101 are screwed into female threads 138 in the ampule cap, the combination illustrated in FIG. 26c is obtained.

Figure 27:
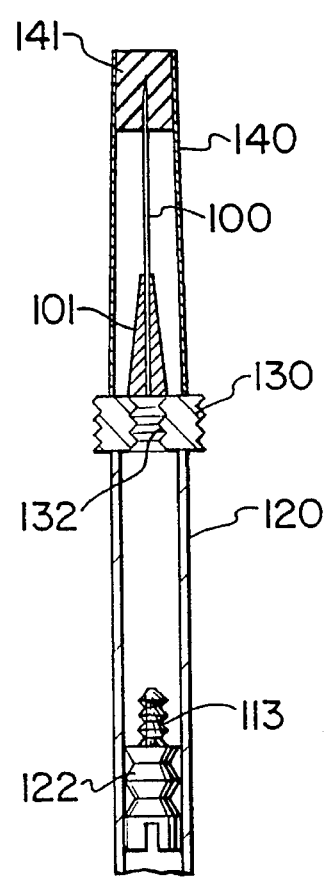
FIG. 27 illustrates a front section view of an alternative design of ampule with ampule cap, needle and needle cover, assembled as a unit for shipping.

FIG. 27 illustrate a front partial section view of an ampule with ampule cap, needle and needle cover, assembled as a unit for shipping. This figure illustrates the needle cover and ampule when sold as a unit in a plastic tube or a bubble pack, or the like. This embodiment does not have the usual soft sealing membrane across the neck of the ampule, but rather, the needle tip is embedded in the rubber, or any other suitable material. This embodiment can be used with a conventional metal dental syringe which has had the needle adapter coupling removed. As seen in FIG. 27, the needle 100, and needle housing 101, are encased in a needle cover 140. The needle cover 140 can have a rubber plug 141 at the top, into which the sharp end of the needle 100 can be embedded in order to maintain a clean needle end. The lower portion of the ampule 120 is the same construction as described previously, with ampule cap 130, covered by the base of the needle cover 140, and plunger 122 and male threads 113 at the top of plunger 122 adapted to engage with female threads 132 of ampule cap 130, when the plunger 122 is fully advanced in the interior of the ampule 120.

Figure 28:
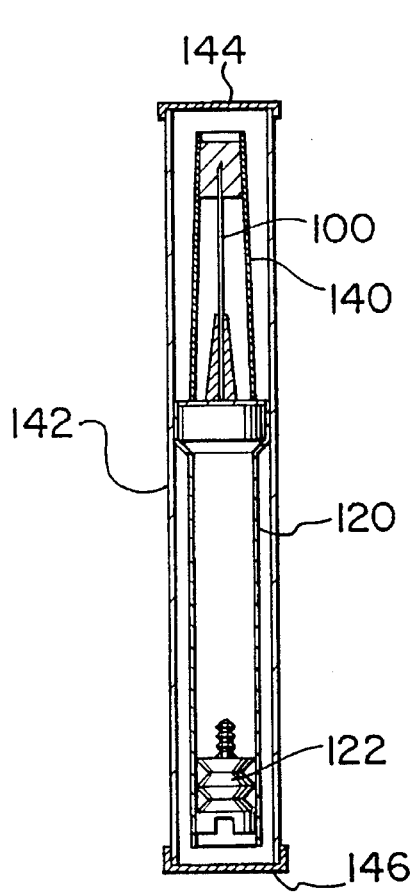
FIG. 28 illustrates a front view of an alternative design of ampule with needle and cover enclosed in a sleeve package with double caps, for shipping.

FIG. 28 illustrates a front view of an alternative embodiment of ampule with needle and cover enclosed in a sleeve package with double caps, for shipping. FIG. 28 shows the ampule 120, and needle 100 encased in a sleeve package 142, which is closed at the top end by top cap 144, and closed at the bottom end by bottom cap 146. Needle cover 140, as previously described, covers needle 100. This embodiment represents the package that is assembled and shipped by the manufacturer.

Figure 29:
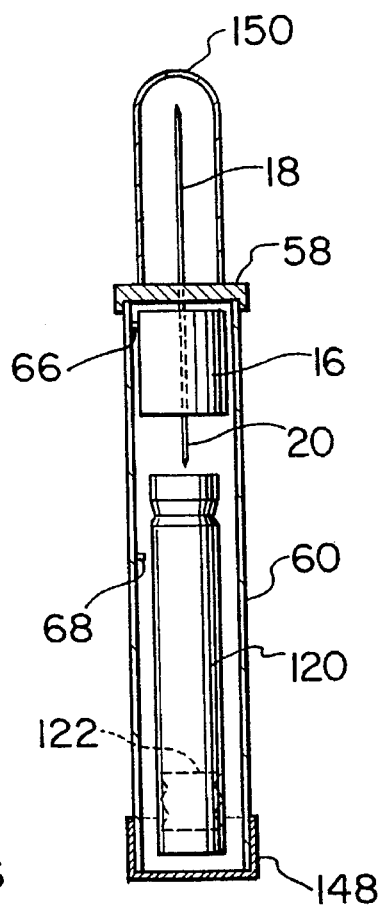
FIG. 29 illustrates a front view of an ampule and needle housing encased in a sleeve, with caps at both ends, and a top cap covering the injection needle for shipping.

FIG. 29 illustrates a front view of a further alternative embodiment of ampule and needle housing encased in a sleeve, with caps at both ends, and a top cap covering the injection needle for shipping. FIG. 29 illustrates an assembly which comprises both a needle hub 16, with injection needle 17, and ampule puncturing needle 28, positioned at the top end of sleeve 60, while the ampule 120, with plunger 122, is located in the lower portion of sleeve 60. The top end of sleeve 60 is closed with collar 58, and a bell-shaped top cap 150, which protects needle 17. The base of sleeve 60 is enclosed with bottom cap 148. It should be noted that if the length of the sleeve 60 proves to be too short to house the needle assembly and the ampule, the bottom cap 148 can be lengthened to accommodate the situation. To use this configuration, the dentist removes the bottom cap 148, and the ampule 120 is loaded into the barrel of the dental syringe. The safety sleeve 60 is placed over the exterior of the syringe barrel, and the needle hub 16 is screwed into the top end of the metal dental syringe. The needle top cap 150 is then removed, thereby exposing injection needle 17 ready for use. The piston 122 is depressed by the plunger of the dental syringe, thereby causing ampule needle 28 to penetrate the top end of ampule 120. The anaesthetic enclosed in the ampule 120 is then expelled through injection needle 17. After use, the plunger 122 is withdrawn, which in turn causes needle hub 16 to release from upper pin 66, and retract to lower pin 68. In this way, needle 17 is withdrawn into the interior of the sleeve 60. The sleeve 60, with the ampule 120, and the withdrawn needle 17, can then be disposed of. The assembly depicted in FIG. 29 is a package that can be assembled by the manufacturer and shipped to the wholesaler or distributor for use by the dentist.

USE AND FUNCTION OF SAFETY SYRINGE

In a typical situation, where a physician, nurse or dentist wishes to use the syringe according to the invention, the physician, nurse or dentist assembles the components of the syringe including thumb plunger, finger grip, pre-filled ampule and needle. The syringe is now ready for injection of the appropriate pharmaceutical or medicinal agent into an appropriate part such as an arm of the patient or anaesthetic into a patient's gums, as the case may be.

On completion of the injection (and as the needle is being withdrawn from the patient) the administrator holds the ampule and finger grip and by withdrawing the thumb plunger draws the needle back into the ampule thereby effectively covering the needle tip. The whole unit is inexpensive and can be discarded. By adopting this post injection methodology, the physician, nurse, dentist and dental assistants are protected from accidental needle stick injuries. It should be noted that both of the handler's hands remain behind the needle at all times. It is never necessary to place a hand ahead of the needle, such as is the case when a conventional cap is placed over a conventional exposed needle.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An ampule safety syringe combination comprising:

(a) an elongated plunger having a first end and a second end, the first end of the plunger having a thumb press thereon, the second end of the plunger having a member thereon for releasably engaging a piston;

(b) a finger grip with an opening therein for slidably receiving therethrough the elongated plunger, and enabling the plunger to be reciprocally moved through the opening in the finger grip, said finger grip having a member thereon for releasably engaging a first end of an ampule, and enabling the second end of the plunger to penetrate through the opening into the interior of the ampule;

(c) a hollow cylindrical ampule having a first end and a second end, the first end of the ampule being proximate and releasably affixed to the finger grip member and the second end opposite the first end having an ampule cap;

(d) a plunger moveable piston having a first end proximate to and releasably connected to the second end of the plunger and a second end of the piston opposite the first end of the piston, the piston being located and slidably held in the interior of the hollow cylindrical ampule, the piston reciprocating along the longitudinal axis within the interior of the hollow cylindrical ampule, the first end of the plunger extending from the first end of the ampule and the finger grip to the exterior of the ampule opposite the second end of the ampule;

(e) an ampule cap affixed to the second end of the ampule in longitudinal axial alignment with and proximate to the second end of the piston and on a side of the second end of the piston opposite the plunger;

(f) a hollow needle with first and second pointed ends and having a needle hub between the first and second pointed ends, the needle and needle hub being located at the second end of the ampule and the ampule cap with the second pointed end of the needle protruding from the second end of the ampule and ampule cap; and (g) a cap and hub fitting with a first end connected to the ampule cap and a second end proximate the second end of the ampule and the second end of the piston, the fitting enabling the needle hub and needle to be releasably affixed to the ampule cap at the second end of the ampule, whereby the first pointed end of the needle penetrates into the interior of the ampule and the second pointed end of the needle extends from the second end of the ampule in a direction opposite to the plunger and the first pointed end of the needle; wherein the first end and the second end of the piston are enclosed in the first end of the ampule, the first end of the piston being releasably engaged by the engagement member on the second end of the plunger, the fitting being proximate to the first end of the needle, and being penetrated by the first pointed end of the needle, the fitting releasably engaging with the cap at the second end of the ampule, the fitting engaging the second end of the piston when contacted by the piston and being detached from the cap and ampule and withdrawn into the interior of the ampule by withdrawal of the plunger and piston, said piston when engaged by the second end of the plunger and moved by the plunger in the direction of the second end of the needle protruding from the second end of the ampule and pumping liquid contents from the interior of the ampule through the second end of the needle, said second end of the piston engaging the first pointed end of the needle and the fitting at the end of travel of the piston and the plunger towards the second end of the ampule, said piston and plunger when moved by the plunger towards the first end of the ampule away from the second end of the ampule, disengaging the fitting from the cap and withdrawing the fitting and the first and second pointed ends of the needle into the interior of the ampule.

2. A syringe as claimed in claim 1 including a liquid seal between the fitting and the needle.

3. A syringe as claimed in claim 2 including a sealing cap holding the ampule cap and the second end of the ampule together.

4. A syringe as claimed in claim 3 including a liquid seal between the ampule cap and the fitting.

5. A syringe as claimed in claim 4 including a liquid seal between the ampule cap and the second end of the ampule.

6. A syringe as claimed in claim 1 wherein the needle hub of the double pointed needle has thereon female threads which are releasably secured to male threads on the second end of the fitting, and the second end of the piston has threads which engage corresponding mating threads on the first end of the fitting when the second end of the piston contacts the first end of the fitting and the plunger and the piston are rotated.

7. A syringe as claimed in claim 6 wherein the second end of the piston has formed thereon female threads which engage male threads on the first end of the fitting, and the first end of the piston has formed thereon female threads which releasably engage male threads on the second end of the plunger, and enable the piston to reciprocally move axially within the interior of the ampule and rotate the piston clockwise or counterclockwise about the longitudinal axis.

8. A syringe as claimed in claim 6 wherein the second end of the piston has thereon male threads which engage corresponding female threads on the first end of the fitting.

9. A syringe as claimed in claim 1 wherein the needle hub of the double pointed needle is a collar which is located at the mid-section of the double pointed needle, the collar releasably engaging with the second end of the fitting.

10. A syringe as claimed in claim 1 wherein the ampule cap has thereon a female thread for releasably engaging the fitting.

11. A syringe as claimed in claim 1 wherein the ampule cap is sealed to the second end of the ampule by a seal.

12. A syringe as claimed in claim 1 wherein the second end of the fitting has thereon a male thread which releasably engages with a corresponding female thread on the first end of the hub of the needle.

13. A syringe as claimed in claim 1 wherein the second end of the fitting has thereon a female thread which releasably engages with a corresponding male thread on the first end of the hub of the needle.

14. A syringe as claimed in claim 1 wherein the hub of the double pointed needle has a male thread on the exterior thereof for releasable engagement with a corresponding female thread on the fitting, said fitting having a female thread thereon for releasably engaging with a corresponding male thread formed on the second end of the piston.

15. A syringe as claimed in claim 1 including a releasable needle cap over the hub and needle.

16. A syringe as claimed in claim 1 including a resilient liquid seal between the exterior of the piston and the interior of the ampule.

17. A syringe as claimed in claim 1 including annular means on the finger grip for releasably engaging the first end of the ampule.

* * * * *